(12) United States Patent
Matano et al.

(10) Patent No.: US 8,293,809 B2
(45) Date of Patent: Oct. 23, 2012

(54) CATIONIC PHOTOPOLYMERIZATION INITIATOR

(75) Inventors: Yoshihiro Matano, Kyoto (JP); Hiroshi Imahori, Kyoto (JP)

(73) Assignee: Kyoto University, Kyoto-Shi (JP)

( * ) Notice: Subject to any disclaimer, the term of this patent is extended or adjusted under 35 U.S.C. 154(b) by 77 days.

(21) Appl. No.: 12/922,278

(22) PCT Filed: Dec. 11, 2008

(86) PCT No.: PCT/JP2008/072545
§ 371 (c)(1),
(2), (4) Date: Sep. 13, 2010

(87) PCT Pub. No.: WO2009/113217
PCT Pub. Date: Sep. 17, 2009

(65) Prior Publication Data
US 2011/0021654 A1     Jan. 27, 2011

(30) Foreign Application Priority Data

Mar. 11, 2008    (JP) .................................. 2008-061205

(51) Int. Cl.
*C08F 2/50* (2006.01)
*C08J 3/28* (2006.01)

(52) U.S. Cl. .......... 522/31; 522/170; 522/184; 522/189; 522/25; 522/168; 522/134; 522/135; 522/143; 522/181; 522/178; 522/29; 522/66

(58) Field of Classification Search .................... 522/25, 522/31, 66, 16, 170, 168, 125, 134, 135, 522/143, 145, 184, 189, 178, 181, 29
See application file for complete search history.

(56) References Cited

U.S. PATENT DOCUMENTS 4,193,799 A * 3/1980 Crivello ........................ 430/319

FOREIGN PATENT DOCUMENTS

| JP | 2-179643 | 7/1990 |
| JP | 3-54202 | 3/1991 |
| JP | 10-218888 | 8/1998 |
| JP | 2000-186071 | 7/2000 |
| JP | 2008-214330 | 9/2008 |

OTHER PUBLICATIONS

Y, Matano, et al.; "A New and Efficient Method for the Preparation of Bismuthonium and Telluronium, Salts Using Aryl- and Alkenylboronic Acids. First Observation of the Chirality at Bismuth in an Asymmetrical Bismuthonium Salt," Organometallics; 1998; vol. 17; No. 20; pp. 4332-4334 and cover sheet (4 Sheets.).

Y. Matano et al.; "Synthesis and Stereochemical Behavior of Unsymmetrical Tetraarylbismuthonium Salts," Organomatellics; 1999; Vo. 16; No. 26; pp. 5668-5681 and cover sheet (5 Sheets.).

Tomonori Shinokura, et al.; "Photochemical Reactions of Tetraarylbismuthonium Salts;" The 34th Symposium on Main Group Element Chemistry; Mar. 13-15, 2007: pp. 311-312 and cover and end sheets. (5 Sheets.).

Y. Matano, et al.; Mosityltriphenylbismuthonium tetrafluorobrate as an efficent bismuth (V) oxidant: remarkable steric effects on reaction rates and chemoselectivities in alcohol oxidation; Tetrahetron Letters; 2007; vol. 48; No. 16; pp. 2885-2888 (4 Sheets.).

Y. Matano, et al.; "Synthesis and Reaction of Unsymmetrical Tetraarylbismuthonium Salts. First Isolation of Bismuthonium Salts Bearing All Different Aryl Groups." Chem Letters; 1998; No. 2; pp. 127-128 (2 sheets.).

Y. Matano, et al.; "Triaryl(1-pyrenyl) bismuthonium Salts; Efficient Photoinitiators for Cationic Polymerization of Oxiranes and a Vinyl Ether;" Org Letters; 2008; vol. 10; No. 11; pp. 2167-2170 and cover sheet (5 sheets).

International Search Report for International Application No. PCT/JP2008/072545 dated Feb. 28, 2009.

* cited by examiner

*Primary Examiner* — Sanza McClendon
(74) *Attorney, Agent, or Firm* — Kratz, Quintos & Hanson, LLP

(57) ABSTRACT

An object of the present invention is to provide a novel cationic photopolymerization initiator that efficiently absorbs light and generates protons. As a means of achieving the object above, a preferred cationic photopolymerization initiator of the present invention includes an initiator comprising a bismuthonium salt represented by the following general formula (II):

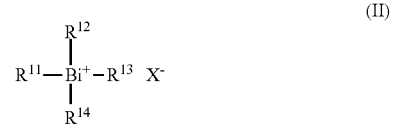

(II)

Wherein
$R^{11}$, $R^{12}$, and $R^{13}$ may be the same or different and are each an optionally substituted monocyclic aryl group or an optionally substituted monocyclic heteroaryl group,
$R^{14}$ is an optionally substituted fused polycyclic aromatic group or an optionally substituted fused polycyclic heterocyclic group, and
$X^-$ is an anion associated with a cation.

8 Claims, No Drawings

CATIONIC PHOTOPOLYMERIZATION INITIATOR

TECHNICAL FIELD

The present invention relates to a novel cationic photopolymerization initiator that efficiently absorbs light and generates protons.

BACKGROUND ART

As is widely known, in recent years, as photo-curable resin compositions for use in printing ink, paint, a coating material, and the like, those utilizing a cationic photopolymerization reaction have attracted attention as well as those utilizing a radical photopolymerization reaction. A photo-curable resin composition utilizing a cationic photopolymerization reaction contains, as main components, a cationic photopolymerizable compound, which contains, for example, an epoxy group, an oxetane group, a vinyl ether group, etc., and a cationic photopolymerization initiator for the polymerization of such a compound. The cationic photopolymerization initiator plays a role in generating protons to initiate a cationic photopolymerization reaction. Well known examples thereof include sulfonium salt based cationic photopolymerization initiators and iodonium salt based cationic photopolymerization initiators.

A cationic photopolymerization initiator is required to have such characteristics that, for example, it efficiently absorbs light, the bond between the cation atom and the carbon atom of the substituent (e.g., $S^+$-Ph bond or $I^+$-Ph bond) is easily cleaved, and the cation atom is susceptible to reduction. Some of the already commercially available cationic photopolymerization initiators are excellent in these characteristics, but there is a demand for a cationic photopolymerization initiator with further improved characteristics.

DISCLOSURE OF THE INVENTION

Problems that the Invention is to Solve

An object of the present invention is to provide a novel cationic photopolymerization initiator that efficiently absorbs light and generates protons.

Means for Solving the Problems

In the course of study in view of the above problems, the present inventors focused attention on bismuth in Group 15, Period 6. The binding energy of bismuth to carbon is small compared with other light elements in the same group, and pentavalent bismuth is easily reduced to trivalent bismuth. Further, the toxicity of bismuth is much lower than heavy elements therearound. The present inventors thus conducted extensive research on the use of bismuth as a cationic photopolymerization initiator. As a result, they found that an onium salt of bismuth (bismuthonium salt) functions effectively as a cationic photopolymerization initiator.

A cationic photopolymerization initiator of the present invention accomplished based on the above findings is, as described in claim 1, characterized by comprising a bismuthonium salt represented by the following general formula (I):

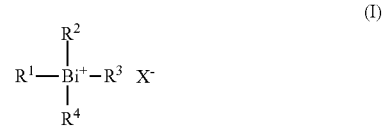

wherein $R^1$ and $R^2$ may be the same or different and are each an optionally substituted monocyclic aryl group or an optionally substituted monocyclic heteroaryl group, $R^3$ and $R^4$ may be the same or different and are each an optionally substituted monocyclic aryl group; an optionally substituted monocyclic heteroaryl group; an optionally substituted fused polycyclic aromatic group; an optionally substituted fused polycyclic heterocyclic group; —CH=$CR^5R^6$, wherein $R^5$ and $R^6$ may be the same or different and are each a hydrogen atom, an optionally substituted alkyl group, an optionally substituted monocyclic aryl group, an optionally substituted monocyclic heteroaryl group, an optionally substituted fused polycyclic aromatic group, or an optionally substituted fused polycyclic heterocyclic group; or —$(CH_2)_n$—$COR^7$, wherein $R^7$ is an optionally substituted alkyl group, an optionally substituted monocyclic aryl group, an optionally substituted monocyclic heteroaryl group, an optionally substituted fused polycyclic aromatic group, or an optionally substituted fused polycyclic heterocyclic group, and n is 1 or 2, and $X^-$ is an anion associated with a cation.

A cationic photopolymerization initiator according to claim 2 is characterized in that in the cationic photopolymerization initiator according to claim 1, $R^1$, $R^2$, and $R^3$ are each an optionally substituted monocyclic aryl group.

A cationic photopolymerization initiator according to claim 3 is characterized in that in the cationic photopolymerization initiator according to claim 1, at least one of $R^3$ and $R^4$ is an optionally substituted fused polycyclic aromatic group.

A cationic photopolymerization initiator according to claim 4 is characterized in that in the cationic photopolymerization initiator according to claim 1, $X^-$ is $PF_6^-$, $SbF_6^-$, $AsF_6^-$, $BF_4^-$, $ORf^-$, $NRf_2^-$, or $B(Ar)_4^-$, wherein Rf is a perfluoroalkylsulfonyl group and Ar is an optionally substituted aryl group.

A method for polymerizing a cationic photopolymerizable compound of the present invention is, as described in claim 5, characterized by using a cationic photopolymerization initiator according to claim 1.

A method according to claim 6 is characterized in that in the method according to claim 5, the cationic photopolymerizable compound is a compound containing at least one member selected from an epoxy group, an oxetane group, and a vinyl ether group.

A photo-curable resin composition of the present invention is, as described in claim 7, characterized by at least comprising a cationic photopolymerizable compound and a cationic photopolymerization initiator according to claim 1.

A cured product of the present invention is, as described in claim 8, characterized by being obtainable by curing a photo-curable resin composition according to claim 7.

A bismuthonium salt of the present invention is, as described in claim 9, characterized by being represented by the following general formula (II):

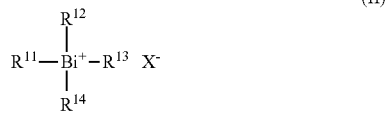

wherein $R^{11}$, $R^{12}$, and $R^{13}$ may be the same or different and are each an optionally substituted monocyclic aryl group or an optionally substituted monocyclic heteroaryl group, $R^{14}$ is an optionally substituted fused polycyclic aromatic group or an optionally substituted fused polycyclic heterocyclic group, and $X^-$ is an anion associated with a cation.

EFFECT OF THE INVENTION

The present invention allows the provision of a novel cationic photopolymerization initiator that efficiently absorbs light and generates protons.

BEST MODE FOR CARRYING OUT THE INVENTION

The cationic photopolymerization initiator of the present invention is characterized by comprising a bismuthonium salt represented by the following general formula (I):

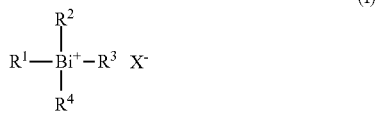

wherein $R^1$ and $R^2$ may be the same or different and are each an optionally substituted monocyclic aryl group or an optionally substituted monocyclic heteroaryl group, $R^3$ and $R^4$ may be the same or different and are each an optionally substituted monocyclic aryl group; an optionally substituted monocyclic heteroaryl group; an optionally substituted fused polycyclic aromatic group; an optionally substituted fused polycyclic heterocyclic group; —CH=$CR^5R^6$, wherein $R^5$ and $R^6$ may be the same or different and are each a hydrogen atom, an optionally substituted alkyl group, an optionally substituted monocyclic aryl group, an optionally substituted monocyclic heteroaryl group, an optionally substituted fused polycyclic aromatic group, or an optionally substituted fused polycyclic heterocyclic group; or —$(CH_2)_n$—$COR^7$, wherein $R^7$ is an optionally substituted alkyl group, an optionally substituted monocyclic aryl group, an optionally substituted monocyclic heteroaryl group, an optionally substituted fused polycyclic aromatic group, or an optionally substituted fused polycyclic heterocyclic group, and n is 1 or 2, and $X^-$ is an anion associated with a cation.

An example of the monocyclic aryl group of the optionally substituted monocyclic aryl group for $R^1$, $R^2$, $R^3$, $R^4$, $R^5$, $R^6$, and $R^7$ is a phenyl group.

Examples of the monocyclic heteroaryl group of the optionally substituted monocyclic heteroaryl group for $R^1$, $R^2$, $R^3$, $R^4$, $R^5$, $R^6$, and $R^7$ include a thienyl group, a pyrrolyl group, a pyridyl group, and a furyl group.

Examples of the fused polycyclic aromatic group of the optionally substituted fused polycyclic aromatic group for $R^3$, $R^4$, $R^5$, $R^6$, and $R^7$ include a naphthyl group, a phenanthryl group, a pyrenyl group, a tetracenyl group, a pentacenyl group, a triphenylenyl group, and a perylenyl group.

Examples of the fused polycyclic heterocyclic group of the optionally substituted fused polycyclic heterocyclic group for $R^3$, $R^4$, $R^5$, $R^6$, and $R^7$ include a carbazolyl group, a phenanthrolyl group, and an acridinyl group.

Examples of the alkyl group of the optionally substituted alkyl group for $R^5$, $R^6$, and $R^7$ include $C_{1-18}$ alkyl groups such as a methyl group, an ethyl group, a propyl group, an isopropyl group, a butyl group, an isobutyl group, a sec-butyl group, a tert-butyl group, a pentyl group, an isopentyl group, a hexyl group, a cyclohexyl group, an octyl group, a decyl group, a dodecyl group, a hexadecyl group, and an octadecyl group.

Examples of substituents of the optionally substituted monocyclic aryl group, the optionally substituted monocyclic heteroaryl group, the optionally substituted fused polycyclic aromatic group, and the optionally substituted fused polycyclic heterocyclic group include $C_{1-18}$ alkyl groups (optionally substituted) such as a methyl group, an ethyl group, a propyl group, an isopropyl group, a butyl group, an isobutyl group, a sec-butyl group, a tert-butyl group, a pentyl group, an isopentyl group, a hexyl group, a cyclohexyl group, an octyl group, a decyl group, a dodecyl group, a hexadecyl group, and an octadecyl group; $C_{2-10}$ alkenyl groups (optionally substituted) such as a vinyl group, an allyl group, a butenyl group, a 2-methyl-1-propenyl group, a 2-methyl-2-propenyl group, and a 1-methyl-1-propenyl group; $C_{1-10}$ alkoxy groups (optionally substituted) such as a methoxy group, an ethoxy group, a propoxy group, a butoxy group, a tert-butoxy group, a pentyloxy group, and a hexyloxy group; aryl groups (optionally substituted) such as a phenyl group and a naphthyl group; heteroaryl groups (optionally substituted) such as a thienyl group, a pyrrolyl group, a pyridyl group, and a furyl group; arylthio groups (optionally substituted) such as a phenylthio group; arylalkyl groups (optionally substituted) such as a benzyl group, a phenylethyl group, a 3-phenylpropyl group, a 1-naphthylmethyl group, a 2-naphthylmethyl group, a 2-(1-naphthyl)ethyl group, a 2-(2-naphthyl)ethyl group, a 3-(1-naphthyl)propyl group, and a 3-(2-naphthyl)propyl group; heteroarylalkyl groups (optionally substituted) such as a 2-pyrrolylmethyl group, a 2-pyridylmethyl group, a 3-pyridylmethyl group, a 4-pyridylmethyl group, a 2-thienylmethyl group, a 2-(2-pyridyl)ethyl group, a 2-(3-pyridyl)ethyl group, a 2-(4-pyridyl)ethyl group, and a 3-(2-pyrrolyl)propyl group; dialkylamino groups such as a dimethylamino group and a diethylamino group; halogen atoms such as fluorine, chlorine, bromine, and iodine; a cyano group; and a nitro group. Examples of substituents of the optionally substituted alkyl group are the above-mentioned alkenyl groups, alkoxy groups, aryl groups, heteroaryl groups, arylthio groups, dialkylamino groups, halogen atoms, a cyano group, a nitro group, etc.

$X^-$ may be, for example, $PF_6^-$, $SbF_6^-$, $AsF_6^-$, $BF_4^-$, $ORf^-$, $NRf_2^-$, or $B(Ar)_4^-$ (Rf is a perfluoroalkylsulfonyl group, and Ar is an optionally substituted aryl group) (an example of the perfluoroalkylsulfonyl group is one having a $C_{1-8}$ perfluoroalkyl moiety, such as a trifluoromethanesulfonyl group, and the optionally substituted aryl group is as defined above). $SbF_6^-$ allows protons to be generated effectively and thus is preferable.

The bismuthonium salt represented by the above general formula (I) may be a known compound based on the research results that have been achieved by the present inventors (see, e.g., Organometallics 1998, 17, 4332-4334). Even in the case where the bismuthonium salt is an unknown compound, it can be synthesized according to the above reference by the following reaction:

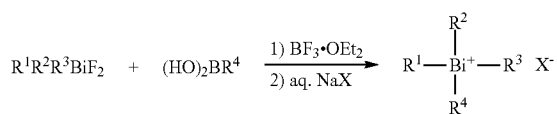

wherein $R^1$, $R^2$, $R^3$, $R^4$, and $X^-$ are as defined above, and

NaX is a sodium salt corresponding to $X^-$.

The cationic photopolymerization initiator of the present invention is suitable for the polymerization of a cationic photopolymerizable compound containing an epoxy group, an oxetane group, a vinyl ether group, etc., for example. The cationic photopolymerization initiator of the present invention is mixed with a cationic photopolymerizable compound to produce a photo-curable resin composition, and the composition is applied to a substrate (e.g., a substrate made of a metal or a synthetic resin; however, the material of the substrate is not limited thereto), for example, and then irradiated with light having a wavelength within a range of 300 to 500 nm for 10 seconds to 3 hours, for example. As a result, protons are effectively generated, and a cationic photopolymerization reaction takes place in the cationic photopolymerizable compound, resulting in a cured product. The amount of the cationic photopolymerization initiator of the present invention present in the photo-curable resin composition is 0.01 to 5 mol %, for example, relative to the cationic photopolymerizable compound. The photo-curable resin composition may contain perylene, acridine orange, acridine yellow, benzoflavin, setoflavin T, pyrene, 9,10-dibutoxyanthracene, 1,2-benzanthracene, phenothiazin, coronene, thioxanthone, fluorenone, benzophenone, anthraquinone, or the like as a sensitizer for promoting the cationic photopolymerization reaction. In such a case, the amount of the sensitizer (preferably having a molar extinction coefficient of, for example, 3000 $M^{-1}$ $cm^{-1}$ or more, and more preferably 5000 $M^{-1}$ $cm^{-1}$ or more) to be added may be about 1/100 to 1/5 relative to the cationic photopolymerization initiator of the present invention (molar ratio). Light to be applied may be suitably selected within a wavelength range of 300 to 700 nm, for example, according to the light absorption characteristics of the sensitizer. The light source may be a high pressure mercury lamp. Alternatively, any of various lasers, a xenon lamp, a halogen lamp, or the like is also usable.

In the present invention, a preferred example of the cationic photopolymerization initiator is an initiator comprising a bismuthonium salt represented by the following general formula (II):

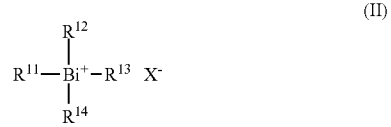

wherein $R^{11}$, $R^{12}$, and $R^{13}$ may be the same or different and are each an optionally substituted monocyclic aryl group or an optionally substituted monocyclic heteroaryl group, $R^{14}$ is an optionally substituted fused polycyclic aromatic group or an optionally substituted fused polycyclic heterocyclic group, and $X^-$ is an anion associated with a cation.

The bismuthonium salt represented by the above general formula (II) has a fused polycyclic aromatic group or a fused polycyclic heterocyclic group bonded to the Bi cation atom, and thus is capable of efficiently absorbing light having a longer wavelength (hv>350 nm) and generating protons. Accordingly, such a bismuthonium salt is suitable for use on the industrial scale, and can also be synthesized easily by the method of the above-mentioned reference.

EXAMPLES

Hereinafter, the present invention will be described in detail with reference to the examples, but the scope of the present invention is not limited to the following descriptions.

Example 1

(A) Synthesis of Bismuthonium Salt (1) Synthesis of tris(4-methylphenyl)(1-pyrenyl)bismuthonium Salt with $SbF_6^-$ as Anion (2a.$SbF_6$)

$BF_3$.$OEt_2$ (0.23 mL, 2.0 mmol) was added dropwise at 0° C. to a methylene chloride solution (10 mL) containing tris (4-methylphenyl)bismuth difluoride (0.52 g, 1 mmol) and 1-pyrenylboric acid (0.27 g, 1.1 mmol), and the mixture was stirred at room temperature for 2 hours. An aqueous solution of $NaSbF_6$ (5.2 g, 20 mmol) wad added thereto, then the resulting two-layer liquid was vigorously stirred for 20 minutes, and the aqueous layer was separated and extracted with methylene chloride. The methylene chloride solution was collected, dried over magnesium sulfate, and passed through a short silica gel column. The eluate was concentrated under reduced pressure, and the resulting solid was recrystallized from methylene chloride—diethyl ether to give the target compound as a pale yellow crystal (yield: 95%, 0.87 g).

Mp 180-182° C.; $^1$H NMR (CDCl$_3$) δ 2.47 (s, 9H), 7.54 (d, 6H, J=7.6 Hz), 7.68 (d, 6H, J=7.6 Hz), 7.84 (d, 1H, J=8.8 Hz), 8.17 (t, 1H, J=7.8 Hz), 8.19 (d, 1H, J=8.8 Hz), 8.22 (d, 1H, J=8.8 Hz), 8.29 (d, 2H, J=8.8 Hz), 8.32 (d, 1H, J=7.8 Hz), 8.35-8.43 (m, 2H); $^{13}$C{$^1$H} NMR (CDCl$_3$) δ 21.6, 123.9, 125.5, 126.9, 127.1, 127.2, 127.4, 127.6, 128.1, 128.9, 130.2, 130.4, 130.9, 131.4, 131.6, 133.2, 133.5, 134.5, 135.3, 143.9; IR (KBr) $v_{max}$ 1584, 1488, 1456, 1392, 1312, 1239, 1207, 1189, 1053, 1004, 849, 795, 709, 656 ($SbF_6^-$), 474 cm$^{-1}$; UV-Vis (CH$_2$Cl$_2$) $\lambda_{max}$ (ε) 342 (27000), 352 (31000), 358 (30000), 377 nm (9600 M$^{-1}$ cm$^{-1}$); MS (MALDI-TOF) m/z 683 ([M-SbF$_6$]$^+$). Anal. Calcd for C$_{37}$H$_{30}$BiF$_6$Sb: C, 48.34; H, 3.29. Found: C, 48.19; H, 3.26.

(2) Synthesis of tris(4-methylphenyl)(1-pyrenyl)bismuthonium Salt with $PF_6^-$ as Anion (2a.$PF_6$)

The compound was synthesized in the same manner as above.

Mp 179-182° C. (decomp); $^1$H NMR (CDCl$_3$) δ 2.46 (s, 9H), 7.54 (d, 6H, J=7.6 Hz), 7.68 (d, 6H, J=7.6 Hz), 7.83 (d, 1H, J=8.8 Hz), 8.15 (t, 1H, J=7.6 Hz), 8.17 (d, 1H, J=8.4 Hz), 8.22 (d, 1H, J=8.8 Hz), 8.27 (d, 2H, J=8.8 Hz), 8.31 (d, 1H, J=7.6 Hz), 8.37 (d, 1H, J=7.6 Hz), 8.40 (d, 1H, J=8.4 Hz); IR (KBr) $v_{max}$ 1584, 1487, 1454, 1392, 1311, 1239, 1208, 1189, 1053, 1005, 900-700 ($PF_6^-$), 707 cm$^{-1}$; UV-Vis ($CH_2Cl_2$) $\lambda_{max}$ ($\epsilon$) 342 (25000), 352 (29000), 358 (28000), 377 nm (8900 M$^{-1}$ cm$^{-1}$); MS (MALDI-TOF) m/z 683 (M$^+$-PF$_6$). Anal. Calcd for $C_{37}H_{30}BiF_6P$: C, 53.63; H, 3.65. Found: C, 53.63; H, 3.52.

(3) Synthesis of tris(4-methylphenyl)(1-pyrenyl)bismuthonium Salt with $BF_4^-$ as Anion (2a.BF$_4$)

The compound was synthesized in the same manner as above.

Mp 231-233° C.; $^1$H NMR (CDCl$_3$) δ 2.45 (s, 9H), 7.50 (d, 6H, J=8.1 Hz), 7.74 (d, 6H, J=8.1 Hz), 7.82 (d, 1H, J=8.8 Hz), 8.14 (t, 1H, J=7.6 Hz), 8.16 (d, 1H, J=9.2 Hz), 8.17 (d, 1H, J=9.2 Hz), 8.26 (d, 1H, J=8.8 Hz), 8.29 (d, 1H, J=7.3 Hz), 8.32 (d, 1H, J=8.1 Hz), 8.36 (d, 1H, J=7.3 Hz), 8.38 (d, 1H, J=8.1 Hz); IR (KBr) $v_{max}$ 1584, 1486, 1463, 1391, 1312, 1241, 1206, 1150-900 (BF$_4^-$), 848, 796, 705 cm$^{-1}$; UV -Vis (CH$_2$Cl$_2$) $\lambda_{max}$ ($\epsilon$) 341 (26000), 352 (29000), 358 (27000), 377 nm (8800 M$^{-1}$ cm$^{-1}$); MS (FAB) m/z 683 (M$^+$-BF$_4$). Anal. Calcd for $C_{37}H_{30}BBiF_4$: C, 57.68; H, 3.92. Found: C, 57.62; H, 3.88.

(4) Synthesis of triphenyl(1-pyrenyl)bismuthonium Salt with $SbF_6^-$ as Anion (2b.SbF$_6$)

The compound was synthesized in the same manner as above.

Mp 176-177° C.; $^1$H NMR (CDCl$_3$, 400 MHz) δ 7.68-7.77 (m, 9H), 7.83 (br-s, 6H), 7.85 (d, 1H, J=8.8 Hz), 8.16-8.24 (m, 3H), 8.29-8.34 (m, 3H), 8.39-8.43 (m, 2H); IR (KBr) $v_{max}$ 1584, 1566, 1475, 1437, 991, 850, 816, 730, 709, 685, 659 (SbF$_6^-$) cm$^{-1}$; UV-Vis (CHCl$_3$) $\lambda_{max}$ ($\epsilon$) 351 (29900), 377 nm (6900M$^{-1}$ cm$^{-1}$); MS (MALDI-TOF) m/z 642 ([M-SbF$_6$]$^+$). Anal. Calcd for $C_{34}H_{24}BiF_6Sb$: C, 46.55; H, 2.76. Found: C, 46.33; H, 2.74.

(B) Photolysis of Bismuthonium Salt

An acetonitrile solution of a bismuthonium salt 2.X (2a.SbF$_6$, 2a.PF$_6$, 2a.BF$_4$, and 2b.SbF$_6$) (0.010 M, 1.5 mL) was placed into a Pyrex® tube, and optionally an excessive amount of hexamethylphosphoric triamide or 2,6-di-tert-butyl-4-methylpyridine was added thereto. Subsequently, through a septum, argon was passed through the solution for 5 minutes. The obtained solution was then irradiated with light using a 250 W ultra high pressure mercury lamp (USHIO SX-UI250HP) as a light source through an aqueous copper sulfate solution filter (5.0 wt %, 5 cm). The bismuthonium salt 2.X was completely consumed in 2 minutes. The resulting reaction mixture was concentrated under reduced pressure, and the residue was dissolved in 0.5 mL of deuterated chloroform containing 1,1,2,2-tetrachloroethane (3.2 μL; internal standard). The product was identified by $^1$H-NMR, and the yield was also determined thereby. The quantum yield of the photolytic reaction was determined by a comparison with a potassium ferrioxalate actinometer (in order to avoid a side reaction of the product, the quantum yield was determined at the time when about 10% of the bismuthonium salt 2.X was consumed). The results are shown in Table 1.

TABLE 1

Photochemical reaction of 2·X in acetonitrile.[a,b]

$Ar_3Bi$-X$^-$  $\xrightarrow{h\nu (>360 \text{ nm})}_{\text{MeCN, 2 min}}$  $Ar_3Bi$ + $Ar_2BiX(HMPA)_2$ +
    2·X                                                             3         4·X

| entry | 2·X | $\Phi_{dec}$ | additive | products (NMR yield/%[c]) |
|---|---|---|---|---|
| 1 | 2a·BF$_4$ | N.d.[d] | none | 3a (30), pyrene (70)[e] |
| 2 | 2a·BF$_4$ | N.d.[d] | HMPA | 3a (25), 4a·BF$_4$ (65), pyrene (75) |
| 3 | 2a·BF$_4$ | 0.20 | py[f] | 3a (70), pyrene (nd), pyH$^+$BF$_4^-$ (90)[f] |
| 4 | 2a·PF$_6$ | 0.22 | HMPA | 3a (20), 4a·PF$_6$ (65), pyrene (80) |
| 5 | 2a·SbF$_6$ | 0.22 | HMPA | 3a (25), 4a·SbF$_6$ (70), pyrene (80) |
| 6 | 2b·SbF$_6$ | 0.22 | HMPA | 3b (20), 4b·SbF$_6$ (70), pyrene (80) |

[a]The photoirradiation was carried out with a high pressure Hg arc lamp through an aqueous CuSO$_4$ filter at room temperature.
[b]a: Ar = p-MeC$_6$H$_4$. b: Ar = Ph.
[c]Determined by $^1$H NMR using an internal standard (1,1,2,2-tetrachloroethane).
[d]Not determined.
[e]Insoluble substances were formed.
[f]py = 2,6-di-tert-buty-4-methylpyridine.

As is obvious from Table 1, as a result of the photolysis of the bismuthonium salt 2.X, tris(4-methylphenyl)bismuthine or triphenylbismuthine and pyrene were obtained as main products. These results were attributed to preferential homolysis of the bond between the ipso-carbon atom of the pyrenyl group and the Bi cation atom due to irradiation with light. In the presence of an excessive amount of hexamethylphosphoric triamide or 2,6-di-tert-butyl-4-methylpyridine, the production of a salt thereof was observed. It was thus revealed that this reaction allows protons to be released into the system. These results confirm the function of a bismuthonium salt 2.X as a cationic photopolymerization initiator.

(C) Cationic Photopolymerization Reaction using Bismuthonium Salt as Cationic Photopolymerization Initiator Using the same container and light irradiation apparatus as used in (B), the following procedure was followed. A monomer (0.8 mL) and a bismuthonium salt 2.X were placed into a sample tube, and argon was passed therethrough for 5 minutes for substitution. This photo-curable resin composition was irradiated with light for a predetermined period of time, and then the reaction mixture was poured into methanol. The precipitate was filtered off and washed with methanol, and then dried under vacuum. The molecular weight of the obtained polymer was determined using a GPC column calibrated with polyethylene oxide standards. The results are shown in Table 2.

TABLE 2

Photoinduced cationic polymerization using 2·X.[a]

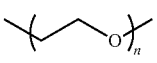

| entry | initiator (mol %) | monomer | time | yield/%[b] | $M_n$ ($M_w/M_n$)[c] |
|---|---|---|---|---|---|
| 1 | none | 5 | 1 min | N.r.[d] | -(-) |
| 2 | 2a·SbF$_6$ (0.1) | 5 | 1 h[e] | N.r.[d] | -(-) |
| 3 | 2a·SbF$_6$ (0.1) | 5 | 1 min | 88 | 9500 (1.2) |
| 4 | 2a·PF$_6$ (0.1) | 5 | 1 min | 41 | 8900 (1.3) |
| 5 | 2a·PF$_6$ (0.1) | 5 | 3 min | 46 | 9000 (1.3) |
| 6 | 2a·PF$_6$ (1) | 5 | 1 min | 58 | 8500 (1.4) |
| 7 | 2a·BF$_4$ (0.1) | 5 | 1 min | <1 | N.d. (N.d.)[f] |
| 8 | 2a·BF$_4$ (1) | 5 | 3 min | <1 | N.d. (N.d.)[f] |
| 9 | 2b·SbF$_6$ (0.1) | 5 | 1 min | 80 | 9000 (1.2) |
| 10 | 3b (0.1) | 5 | 1 min | N.r.[d] | -(-) |
| 11 | 2a·SbF$_6$ (0.1) | 6 | 1 min[g] | 48 | 7800 (1.2) |
| 12 | 2a·SbF$_6$ (0.5) | 6 | 1 min[g] | 59 | 8400 (1.2) |
| 13 | 2a·SbF$_6$ (0.1) | 7 | 1 min | 90 | 15800 (1.4) |
| 14 | 2b·SbF$_6$ (0.1) | 7 | 1 min | 85 | 16100 (1.4) |
| 15 | 2a·SbF$_6$ (0.1) | 8 | 1 min | 74 | 16600 (1.7) |

[a]The photoirradiation was carried out with a high pressure Hg arc lamp through an aqueous CuSO$_4$ filter at room temperature.
[b]Isolated yields of polymers.
[c]$M_n$ and $M_w$ were determined by GPC (JAIGEL-5H—AF, eluted with CHCl$_3$) using poly (ethylene glycol) as a standard.
[d]No reaction.
[e]No irradiation.
[f]Not determined.
[g]After irradiation, the reaction mixture was stood in the dark for 30 min.

monomer:

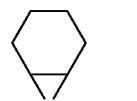

5

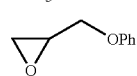

6

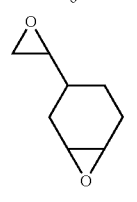

7

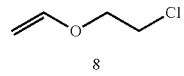

8

As is obvious from Table 2, when the bismuthonium salt 2.X was used as a cationic photopolymerization initiator, it could be confirmed that a polymer was produced by a cationic photopolymerization reaction of the monomer.

Example 2

Comparison (I) Between Effects of Cationic Photopolymerization Initiator Comprising Bismuthonium Salt And of Existing Cationic Photopolymerization Initiator on Cationic Photopolymerization Reaction Using Sensitizer This experiment was conducted in the same manner as in Example 1, (C), using cyclohexene oxide as a monomer and, as a bismuthonium salt, a tetrakis(4-methylphenyl)bismuthonium salt with SbF$_6^-$ as an anion (synthesized from tris(4-methylphenyl)bismuth difluoride and 4-methylphenylboric acid in the same manner as in Example 1, (A); the physicochemical properties thereof are as shown below) (0.1 mol % relative to the monomer). In this experiment, perylene in 1/10 the amount of the bismuthonium salt (molar ratio) was added as a sensitizer. The results are shown in Table 3. Table 3 also shows the results of an experiment conducted in the same manner using as an existing cationic photopolymerization initiator a tris(4-methylphenyl)sulfonium salt with SbF$_6^-$ as an anion.

TABLE 3

| Initiator | Time (min) | Yield/%[a] | $M_n$ ($M_w/M_n$)[b] |
|---|---|---|---|
| Bismuthonium salt | 0.5 | 38 | 8700 (1.2) |
|  | 1.0 | 86 | 7900 (1.2) |
| Sulfonium salt | 0.5 | 22 | 7500 (1.2) |
|  | 1.0 | 78 | 6900 (1.2) |

[a],[b]the same as in Table 2

As is obvious from Table 3, it was revealed that in a cationic photopolymerization reaction using a sensitizer, a cationic photopolymerization initiator comprising a bismuthonium salt is superior to an existing cationic photopolymerization initiator in terms of yield and degree of polymerization.

(Reference)

Physicochemical properties of tetrakis(4-methylphenyl)bismuthonium salt with SbF$_6^-$ as anion Mp 175-178° C.; $^1$H NMR δ 2.46 (s, 12H), 7.52 (d, 8H, J=8.0 Hz), 7.58 (d, 8H, J=8.0 Hz); $^{13}$C NMR δ 21.6, 131.4, 133.4, 135.4, 143.9; IR (KBr) $v_{max}$ 1581, 1488, 1447, 1392, 1312, 1208, 1188, 1120, 1054, 1004, 835, 794, 656 (SbF$_6^-$), 473 cm$^{-1}$; MS (MALDI TOF) m/z 573 (M$^+$-SbF$_6$). Anal. Calcd for C$_{28}$H$_{28}$BiF$_6$Sb: C, 41.56; H, 3.49. Found: C, 41.43; H, 3.32.

Example 3

Comparison (II) Between Effects of Cationic Photopolymerization Initiator Comprising Bismuthonium Salt and of Existing Cationic Photopolymerization Initiator on Cationic Photopolymerization Reaction Using Sensitizer Cyclohexene oxide was placed as a monomer into a sample tube. Further, 10 mM of a tetrakis(4-methylphenyl)bismuthonium salt with SbF$_6^-$ as an anion as a bismuthonium salt and 1 mM of perylene as a sensitizer were added thereto, and argon was passed therethrough for 5 minutes for substitution. A solution of this photo-curable resin composition was irradiated with light (hv>436 nm) for a predetermined period of time using a 250 W ultra high pressure mercury lamp (USHIO SX-UI250HP) as a light source through an aqueous copper sulfate solution filter (5.0 wt %, 5 cm) and a cut filter (product of HOYA: L42). The reaction mixture was poured into methanol. The precipitate was filtered off and washed with methanol, and then dried under vacuum. The molecular weight of the obtained polymer was determined using a GPC column calibrated with polyethylene oxide standards. The results are shown in Table 4. Table 4 also shows the results of an experiment conducted in the same manner using as an existing cationic photopolymerization initiator a tris(4-methylphenyl)sulfonium salt with SbF$_6^-$ as an anion.

TABLE 4

| Initiator | Time (min) | Yield/%[a] | $M_n$ $(M_w/M_n)$[b] |
|---|---|---|---|
| Bismuthonium salt | 1.0 | 20 | 8000 (1.2) |
|  | 3.0 | 81 | 7900 (1.2) |
|  | 5.0 | 80 | 8000 (1.2) |
| Sulfonium salt | 1.0 | 10 | 8300 (1.2) |
|  | 3.0 | 64 | 7600 (1.2) |
|  | 5.0 | 78 | 7900 (1.1) |

[a,b]the same as in Table 2

As is obvious from Table 4, it was revealed that as compared with an existing cationic photopolymerization initiator, a cationic photopolymerization initiator comprising a bismuthonium salt results in a higher photon yield in a cationic photopolymerization reaction using a sensitizer, and the reaction proceeds within a shorter period of time.

Example 4

Comparison (III) Between Effects of Cationic Photopolymerization Initiator Comprising Bismuthonium Salt and of Existing Cationic Photopolymerization Initiator on Cationic Photopolymerization Reaction Using Sensitizer 2-(Phenoxymethyl)oxirane was placed as a monomer into a sample tube. Further, 10 mM of a tetrakis(4-methylphenyl) bismuthonium salt with $SbF_6^-$ as an anion as a bismuthonium salt and 1 mM of perylene as a sensitizer were added thereto, and argon was passed therethrough for 5 minutes for substitution. A solution of this photo-curable resin composition was irradiated with light (hv>360 nm) for 1 minute using a 250 W ultra high pressure mercury lamp (USHIO SX-UI250HP) as a light source through an aqueous copper sulfate solution filter (5.0 wt %, 5 cm), and then allowed to stand in a dark room for 30 minutes. Subsequently, the reaction mixture was poured into methanol. The precipitate was filtered off and washed with methanol, and then dried under vacuum. The molecular weight of the obtained polymer was determined using a GPC column calibrated with polyethylene oxide standards. The results are shown in Table 5. Table 5 also shows the results of an experiment conducted in the same manner using as an existing cationic photopolymerization initiator a tris(4-methylphenyl)sulfonium salt with $SbF_6^-$ as an anion.

TABLE 5

| Initiator | Time (min) | Yield/%[a] | $M_n$ $(M_w/M_n)$[b] |
|---|---|---|---|
| Bismuthonium salt | 1 + 30 (dark) | 60 | 8000 (1.3) |
| Sulfonium salt | 1 + 30 (dark) | 64 | 8500 (1.2) |

[a,b]the same as in Table 2

As is obvious from Table 5, it was revealed that in this experiment system, a cationic photopolymerization initiator comprising a bismuthonium salt and an existing cationic photopolymerization initiator have similar effects.

Example 5

Comparison (IV) Between Effects of Cationic Photopolymerization Initiator comprising Bismuthonium Salt and of Existing Cationic Photopolymerization Initiator on Cationic Photopolymerization Reaction Using Sensitizer (2-Chloroethoxy)ethylene was placed as a monomer into a sample tube. Further, 10 mM of a tetrakis(4-methylphenyl) bismuthonium salt with $SbF_6^-$ as an anion as a bismuthonium salt and 1 mM of perylene as a sensitizer were added thereto, and argon was passed therethrough for 5 minutes for substitution. A solution of this photo-curable resin composition was irradiated with light (hv>360 nm) for a predetermined period of time using a 250 W ultra high pressure mercury lamp (USHIO SX-UI250HP) as a light source through an aqueous copper sulfate solution filter (5.0 wt %, 5 cm). Subsequently, the reaction mixture was poured into methanol. The precipitate was filtered off and washed with methanol, and then dried under vacuum. The molecular weight of the obtained polymer was determined using a GPC column calibrated with polyethylene oxide standards. The results are shown in Table 6. Table 6 also shows the results of an experiment conducted in the same manner using as an existing cationic photopolymerization initiator a tris(4-methylphenyl)sulfonium salt with $SbF_6^-$ as an anion.

TABLE 6

| Initiator | Time (min) | Yield/%[a] | $M_n$ $(M_w/M_n)$[b] |
|---|---|---|---|
| Bismuthonium salt | 0.5 | 34 | 13000 (1.4) |
|  | 1.0 | 68 | 12900 (1.4) |
| Sulfonium salt | 0.5 | 20 | 14000 (1.5) |
|  | 1.0 | 60 | 12800 (1.4) |

[a,b]the same as in Table 2

As is obvious from Table 6, it was revealed that in a cationic photopolymerization reaction using a sensitizer, a cationic photopolymerization initiator comprising a bismuthonium salt is superior to an existing cationic photopolymerization initiator in terms of yield and degree of polymerization.

Industrial Applicability

The present invention has an industrial applicability in the point that it can provide a novel cationic photopolymerization initiator that efficiently absorbs light and generates protons.

The invention claimed is:

1. A cationic photopolymerization initiator characterized by comprising a bismuthonium salt represented by the following general formula (I):

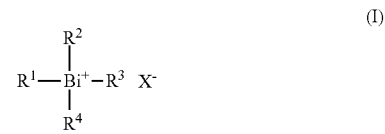

(I)

wherein
$R^1$, $R^2$ and $R^3$ may be the same or different and are each an optionally substituted monocyclic aryl group or an optionally substituted monocyclic heteroaryl group,
$R^4$ is an optionally substituted fused polycyclic aromatic group or an optionally substituted fused polycyclic heterocyclic group and
$X^-$ is an anion associated with a cation.

2. A cationic photopolymerization initiator according to claim 1, characterized in that $R^1$, $R^2$, and $R^3$ are each an optionally substituted monocyclic aryl group.

3. A cationic photopolymerization initiator according to claim 1, characterized in that $X^-$ is $PF_6^-$, $SbF_6^-$, $AsF_6^-$, $BF_4^-$, $ORf^-$, $NRf_2^-$, or $B(Ar)_4^-$, wherein Rf is a perfluoroalkylsulfonyl group and Ar is an optionally substituted aryl group.

4. A method for polymerizing a cationic photopolymerizable compound characterized by using a cationic photopolymerization initiator according to claim 1.

5. A method according to claim 4, characterized in that the cationic photopolymerizable compound is a compound containing at least one member selected from an epoxy group, an oxetane group, and a vinyl ether group.

6. A photo-curable resin composition characterized by at least comprising a cationic photopolymerizable compound and a cationic photopolymerization initiator according to claim 1.

7. A -cured product characterized by being obtainable by curing a photo-curable resin composition according to claim 6.

8. A. bismuthonium salt characterized by being represented by the following general formula (II):

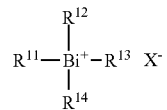

wherein
$R^{11}$, $R^{12}$, and $R^{13}$ may be the same or different and are each an optionally substituted monocyclic aryl group or an optionally substituted monocyclic heteroaryl group, $R^{14}$ is an optionally substituted used polycyclic aromatic group or an optionally substituted fused polycyclic heterocyclic group, and $X^-$ is an anion. associated with a cation.

* * * * *